United States Patent [19]
Harnish et al.

[11] Patent Number: 5,980,863
[45] Date of Patent: Nov. 9, 1999

[54] MANGANESE COMPOSITIONS AND METHODS FOR MRI

[75] Inventors: Phillip P. Harnish; Peter R. Seoane, both of Downingtown; Adele R. Vessey, Elverson, all of Pa.

[73] Assignee: Eagle Vision Pharmaceutical Corporation, Chester Springs, Pa.

[21] Appl. No.: 09/184,835

[22] Filed: Nov. 2, 1998

[51] Int. Cl.$^6$ .................................................. A61B 5/055
[52] U.S. Cl. ............................................................ 424/9.36
[58] Field of Search ........................... 424/9.36; 600/420; 436/173

[56] References Cited

U.S. PATENT DOCUMENTS

| | | | |
|---|---|---|---|
| 4,647,447 | 3/1987 | Gries et al. | 424/9 |
| 4,719,098 | 1/1988 | Weinmann et al. | 424/9 |
| 4,915,933 | 4/1990 | Matwiyoff | 424/9 |
| 4,986,980 | 1/1991 | Jacobsen | 424/9 |
| 5,078,986 | 1/1992 | Bosworth et al. | 424/9.36 |
| 5,082,649 | 1/1992 | Van Deripe | 424/9 |
| 5,250,284 | 10/1993 | Krongrad | 424/9.36 |
| 5,401,492 | 3/1995 | Kellar et al. | 424/9.36 |
| 5,458,870 | 10/1995 | Deutsch et al. | 424/9.322 |
| 5,525,326 | 6/1996 | Unger | 424/9.36 |
| 5,534,240 | 7/1996 | Hasegawa et al. | 424/9.36 |
| 5,716,598 | 2/1998 | Golman et al. | 424/9.36 |

FOREIGN PATENT DOCUMENTS 0 308 983  3/1989  European Pat. Off. .

OTHER PUBLICATIONS

S. Schaeffer et al., "In Vivo Nuclear Magnetic Resonance Imaging of Myocardial Perfusion Using the Paramagnetic Contrast Agent Manganese Gluconate," *JACC 14(2)*, pp. 472–480 (1989).

S. Schaeffer et al., "Nuclear Magnetic Resonance Imaging of Partial Coronary Artery Occlusion" (Abstract), *Soc Magn Res in Med*, p. 329 (1987).

S. Schaeffer et al., "Assessment of myocardial perfusion in vivo using nuclear magnetic resonance imaging" (Abstract), *Magn Reson Imag*, p. 133 (1987).

S. Schaeffer et al., "Contrast–Enhanced Magnetic Resonance Imaging of Hypoperfused Myocardium," *Investigative Radiology 26*, pp. 551–556 (1991).

M. Spiller et al., "Longitudinal Proton Relaxation Rates in a Rabbit Tissues after Intravenous Injection of Free and Chelated $Mn^{2+}$," *Mag Reson in Med 8*, 293–313 (1988).

M.E. Bernadino et al., "Safety and Optimum Concentration of a maganese Chloride–based Oral MR Contrast Agent, " *JMRI 4(6)*, pp. 872–876 (1994).

*Primary Examiner*—Gary E. Hollinden
*Attorney, Agent, or Firm*—Heslin & Rothenberg, P.C.

[57] ABSTRACT

An MRI contrast medium of improved safety and efficacy is disclosed. The composition includes a source of calcium ions and a source of manganese ions in a ratio of from 2:1 to 40:1 in a vehicle suitable for parenteral administration. A method of enhancing an MRI signal in a mammalian tissue with the foregoing composition is also provided.

27 Claims, 3 Drawing Sheets

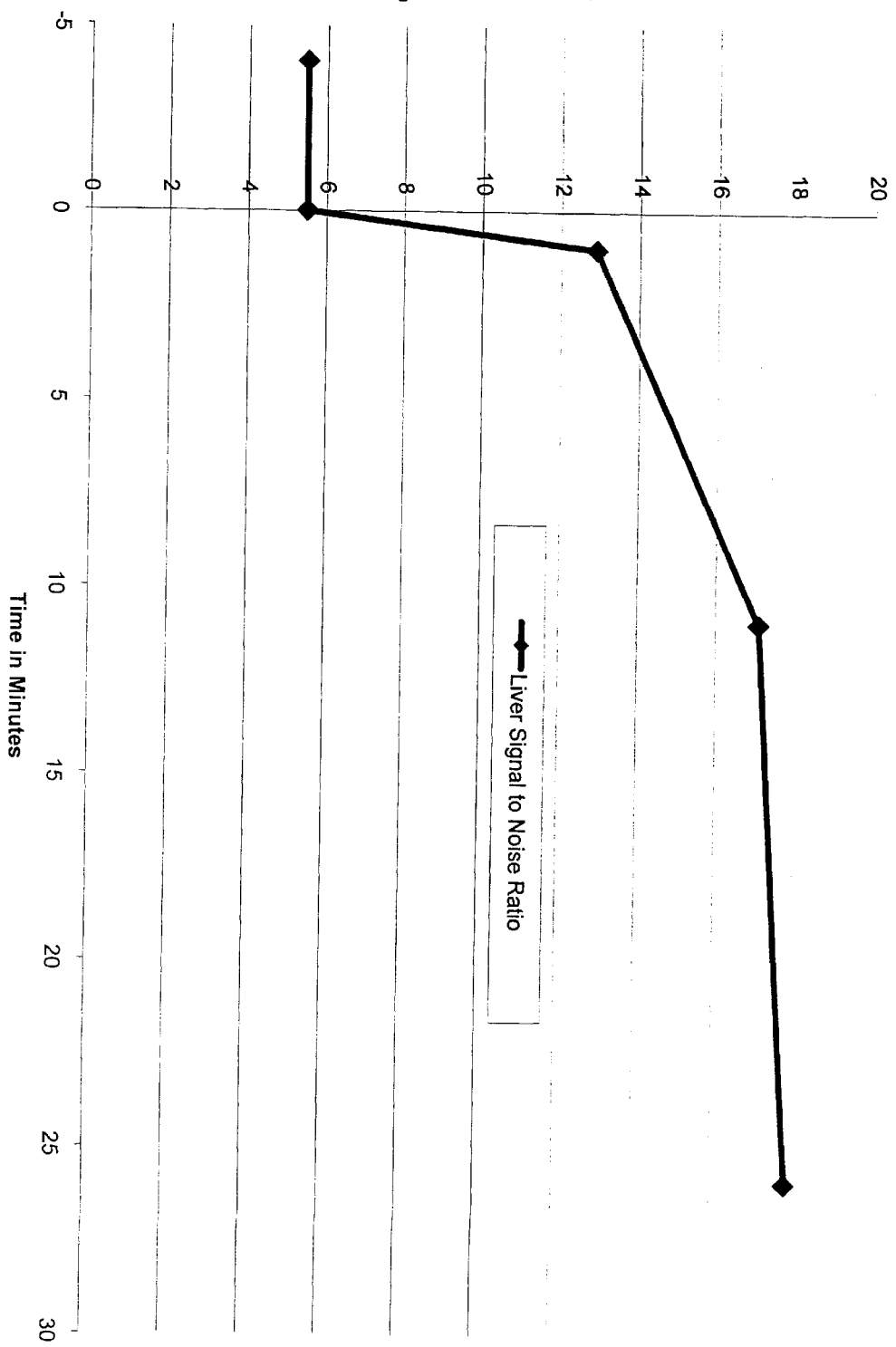

MANGANESE COMPOSITIONS AND METHODS FOR MRI

FIELD OF THE INVENTION

The invention relates to compositions and methods for enhancing magnetic resonance images of tissues, systems and organs.

BACKGROUND OF THE INVENTION

Magnetic resonance imaging enables noninvasive visualization of tissues and organs of the human body. Contrast in the images generated may be enhanced through the use of an agent that alters the relaxation of water in the tissues of interest relative to bulk water. Species with unpaired electrons, such as the paramagnetic transition and lanthanide metal ions, may be used for this purpose. Manganese chloride was investigated as a contrast agent by Lauterbur and by Wolf in animal models. Both investigators demonstrated significant image enhancement of the liver and other organs (but not blood) through the use of manganese chloride, but determined that the potential clinical utility of the agent was limited by acute cardiac toxicity. Development of contrast agents based on other paramagnetic metal ions is similarly constrained by toxicity and solubility. For instance, gadolinium chloride, acetate and sulfate demonstrate poor tolerability, including symptoms of heavy metal poisoning and accumulation of gadolinium in the liver, spleen and bone.

Chelates of paramagnetic transition and lanthanide metals have been used with some success in diagnostic imaging to overcome both the toxicity and solubility problems. (See U.S. Pat. No. 4,647,447.) Application of this technology has enabled the development of several gadolinium based MR contrast agents including Gd-DTPA (Magnevist™, Schering), Gd-DTPA-BMA (Omniscan™, Nycomed Amersham PL), Gd-HP-DO3A (Prohance™, Bracco Diagnostics) and Gd-DOTA (Dotarem™, Guerbet), as well as the manganese-based contrast agent MnDPDP (Teslascan™, Nycomed Amersham PL). There are, however, drawbacks associated with the use of chelation to solve problems of toxicity. Metals ions are not irreversibly held in chelate complexes, but are subject to equilibrium between bound and free states. In vivo, this equilibrium is further complicated by equilibria between the chelator and endogenous metal ions as well as between the paramagnetic metal ion and endogenous ligands. Greis, in U.S. Pat. No. 5,098,692 and Bosworth, in U.S. Pat. No. 5,078,986 disclose the use of excess chelator to minimize the amount of free metal ion in chelate-based diagnostic compositions. Nonetheless, the potential for the dissociation of metal ion from the complex remains. The free chelator, either excess or released, may introduce additional toxicity on its own or through chelation of those endogenous metal ions that are required as cofactors for essential enzymes or for other biological functions. Unfortunately, chelates also demonstrate reduced solution relaxivity relative to the free metal ions. The interaction of paramagnetic metal ions with water molecules, which shortens proton relaxation time relative to bulk water and gives rise to signal enhancement, is obtunded by chelation, since the same sites of metal-water interaction are used to form the non-covalent associations between metal and chelate. Thus chelation provides safety at the price of reduced imaging efficacy (compared to the free metal ion). In practice this loss of efficacy may be as high as 60–80%.

Manganese chelate image enhancement agents are known: e.g MnDPDP, MnDTPA, MnEDTA and derivatives, Mn porphyrins such as $MnTPPS_4$, and fatty acyl DTPA derivatives. These manganese chelates are not known to bind to endogenous macromolecules, as is the case for manganese ion. As a consequence, the enhanced efficacy seen for Mn ion following macromolecular association is seen for Mn chelates only as a function of the rate at which and the extent to which the manganese ion dissociates from the complex. This results in the need for increased dosing of Mn chelates relative to free Mn ion. The dose must be additionally increased to make up for losses due to renal excretion of the chelate during the time course of the diagnostic examination. In a variation on chelation, Quay (European patent application 308983) has described the use of manganese amino acid coordination complex solutions. This application also discusses the addition of calcium ions to the manganese amino acid solutions at levels up to 0.75 mole equivalents relative to manganese.

About ten years ago, Schaefer et al investigated a mixture of Mn++ and Ca++ salts in the form of manganese gluconate and calcium gluconate in a one to one mole ratio, administered intravenously to dogs, for cardiac perfusion imaging. Although the agent discriminated normally perfused from ischemic tissue, Schaefer et al also noted acute cardiotoxicity similar to that seen with manganese chloride alone. The authors suggested that a possible way around the observed adverse cardiac effects might be to employ a chelate rather than a salt of manganese. No further studies employing manganese gluconate and calcium gluconate or other salts or complexes providing Mn++ and Ca++ in a higher ratio than one- to-one have subsequently appeared.

U.S. Pat. Nos. 5,525,326 and 5,716,598 describe oral manganese formulations for imaging of the gastrointestinal tract and for liver imaging; the latter takes advantage of the fact that the blood supply from the GI tract passes through the liver, which removes the manganese from the blood stream prior to return of the blood to the heart. Additional oral agents have been investigated, including manganese polymers, manganese impregnated molecular sieves, manganese clays and foodstuffs with high manganese content, such as blueberry juice. In general, cardiovascular safety is achieved for these agents at the expense of limiting the diagnostic utility of the agents to MR examination of the GI tract and in some cases, the liver. The administration of manganese in nanoparticulate form has been described in U.S. Pat. No. 5,401,492. Other particulate approaches include sequestration of Mn compounds in liposomes and metal clusters, such as manganese oxalate and manganese hydroxyapatite. Particulate agents are useful for a limited number of diagnostic applications, namely, the gastrointestinal tract and organs, such as the liver and the spleen, that are involved in the uptake and sequestration of blood borne particles.

Thus it would be useful to have an agent for diagnostic imaging of tissues, systems and organs, particularly in humans, that would increase the contrast in an MR image without giving rise to problems of toxicity. It would also be useful to have an agent that could be employed for a wide variety of tissues, systems and organs that are physiologically remote from the gastrointestinal tract.

SUMMARY OF THE INVENTION

This need is satisfied, the limitations of the prior art overcome, and other benefits realized in accordance with the principles of the present invention, which in one aspect relates to a diagnostic composition comprising a source of a diagnostically effective quantity of Mn++ ion, a source of Ca++ ion and a pharmaceutically acceptable carrier for parenteral administration. The Ca++ ion is present in a molar ratio of from 2:1 to 40:1 with respect to the Mn++ ion. Preferred sources of Mn++ are manganese salts, such as manganese acetate, chloride, gluconate, gluceptate, lactate and sulfate or mixtures thereof Manganese gluconate or manganese gluceptate are most preferred sources of Mn++. Preferred sources of Ca++ are calcium salts, such as calcium acetate, chloride, gluconate, gluceptate, and lactate or mixtures thereof Calcium gluconate and calcium gluceptate are most preferred sources of Ca++. The molar ratio of calcium to manganese is preferably from 4:1 to 20:1 and most preferably from 8:1 to 10:1. One embodiment of the composition aspect of the invention is a unit dosage form comprising a salt of manganese containing from 5 mg to 200 mg of manganese, a salt of calcium containing from 20 mg to 3 g of calcium, and a vehicle suitable for parenteral injection.

In another aspect, the invention relates to a method for enhancing a magnetic resonance image of a mammalian tissue, organ or system. The method comprises administering to a mammal a diagnostically effective amount of a source of Mn++ ion together with from 2 to 200 molar equivalents of a source of Ca++ ions. The preferred sources of Mn++ and Ca++ are as before. The sources of manganese and calcium may be administered intravenously at 1 $\mu$mol of Mn++ per kg body weight to 100 $\mu$mol of Mn++ per kg body weight and 2 $\mu$mol of Ca++ per kg body weight to 1400 $\mu$mol of Ca++ per kg body weight. The method is applicable to the visualization of liver, kidney, pancreas, adrenal glands, heart, brain, salivary glands, gastrointestinal mucosa, uterus, tumors, the biliary system and the circulatory system. The source of Mn++ and the source of Ca++ may be administered simultaneously or separately, with Ca administration preceding Mn administration by up to 30 minutes.

BRIEF DESCRIPTION OF THE DRAWINGS

Numerous advantages and features of the present invention will become readily apparent from the following detailed description of preferred embodiments, the appended claims and the accompanying drawings wherein:

FIG. 3 is a graph of the ratio of MRI signal-to-noise as a function of time (in minutes) following administration of a composition of the invention.

DETAILED DESCRIPTION OF THE INVENTION

Figure 1:
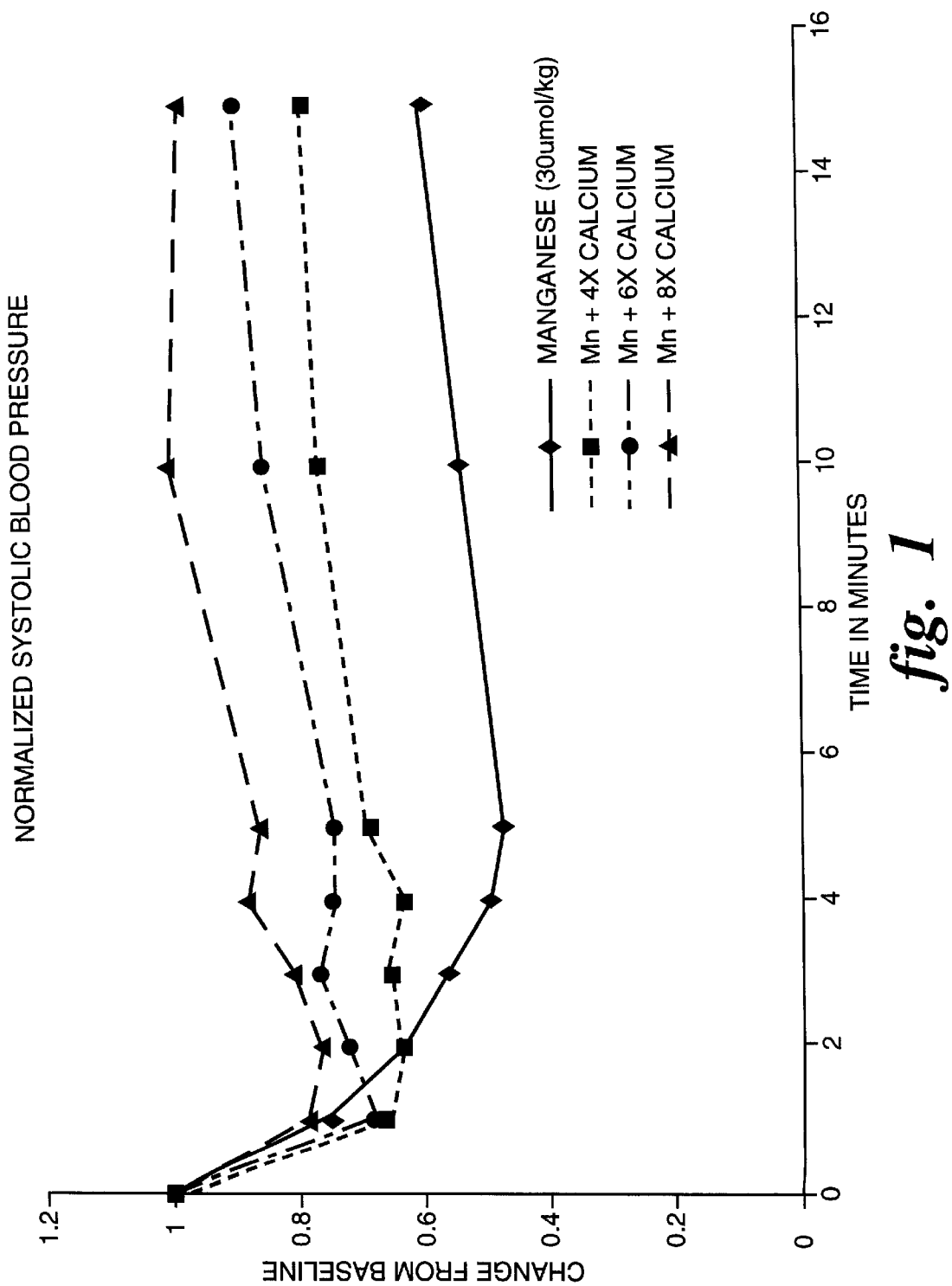
FIG. 1 is a graph of normalized systolic blood pressure in which the change from baseline (in percent) is plotted as a function of time (in minutes)

Although preferred embodiments of the invention are described below, it should be understood that the present disclosure is to be considered as an exemplification of the principles of this invention and is not intended to limit the invention to the embodiments illustrated.

We have found that, for the case of manganese salts, formulation and/or administration with sources of calcium (II) results in a contrast agent with significantly improved safety, as long as the ratio of calcium to manganese is at least 2:1. Although in principle one could use any ratio higher than 2:1, in practice, however, the ratio of Ca ion to Mn ion employed for any given dose of Mn ion will be limited by Ca toxicity. For example, assuming LD50 values following rapid IV administration of 138 $\mu$mol/kg and 1819 $\mu$mol/kg for Mn ion and Ca ion respectively, for low doses of Mn, one may contemplate the use of quite large molar excesses of Ca ion before toxicity is seen. Thus at a Mn ion dose of 1 $\mu$mol/kg, a Ca ion to Mn ion ratio of as high 1800:1 could be considered without exceeding the Ca ion LD50; more conservatively, a ratio of 180:1 could be contemplated by approaching $\frac{1}{10}^{th}$ of the Ca ion LD50. If, however, the Mn ion dose is increased to 10 $\mu$mol/kg, the ratio of Ca to Mn will not exceed 18:1 if the conservative approach of remaining below $\frac{1}{10}^{th}$ of the Ca ion LD50 is followed. In practice, it is not necessary to approach maximal amounts of added Ca to achieve a significant safety benefit. The particular ratio of Ca ion to Mn ion depends on the indication, the dose required to achieve efficacy and the desired safety margin (therapeutic index) for the Mn/Ca composition. As a consequence of the invention, several advantages are realized. For example, improved utilization of the paramagnetic properties of manganese is achieved without the reduction in relaxivity or loss of agent through renal excretion associated with chelation. Manganese chelates demonstrate different phamacokinetics and pharmacodynamics for the manganese metal and the chelator components, suggesting dechelation. In such cases, one may see toxicity mediated through both the metal and the chelator. In contrast, in the present invention, levels of Mn ion that would otherwise not be considered to be physiologically tolerable may be safely reached.

The compositions and methods of the invention are of utility in imaging a variety of metabolically active organs, in particular the liver, kidney, pancreas, heart, and adrenal glands. Manganese contrast enhancement is also useful for imaging of the gastrointestinal mucosa, uterus, salivary glands, brain, the biliary tree, and tumors. Although applicants do not intend that the invention be restricted to a particular theory, it appears from the results that a macromolecular association between Mn ion and one or more native body protein(s)/component(s) is responsible for the superior relaxivity noted. It is known that Mn ion binds to human serum albumin, alpha.2-macroglobulin, transferrin, and other blood proteins with a concomitant increase in Mn relaxivity due to macromolecular association. This relaxivity increase, coupled with the increased concentration of free manganese in the blood available for macromolecular association through the use of the compositions of this invention, provides an increase in signal intensity sufficient to allow even vascular imaging at biologically tolerable doses of Mn++. In fact, on an equimolar basis, the Mn++/Ca++ compositions of the invention are approximately 20-fold more effective than the current gold standard gadolinium chelates in enhancing MR signal intensity in the blood, without suffering from contrast agent extravasation and rapid signal to noise degradation typical of extracellular fluid agents. Improved therapeutic ratio is demonstrated through an increase of the $LD_{50}$ for Mn ion from 138 $\mu$mol/kg to 220 $\mu$mol/kg on administering a 10:1 Ca++/Mn++ composition.

It appears that, although unnecessary, toxicity modifiers could be used with the compositions of the invention. Thus one could contemplate, for example, liposomal sequestration, etc, where there is the potential for equilibration between bound and free metal ion in vivo. In addition, various rates of administration could provide different advantages. For example, by effectively reducing the instantaneous Mn concentration, slower administration of the agents described in this invention may further enhance the therapeutic (diagnostic) index of the agents or allow for the safe administration of larger doses. Thus the compositions of the invention may be administered intravenously as a bolus or as an infusion over a period of time. Commonly, though not necessarily, the infusion will be over a period of 1 minute to 30 minutes. Larger doses improve the imaging of organs, such as the heart, that take up manganese less efficiently than does liver. Similarly, since Mn is effectively and efficiently cleared from the blood, primarily by the liver, one may slow the rate of administration to increase the duration of signal intensity enhancement of blood without increasing total dose.

In a preferred embodiment, Mn gluconate/Ca gluconate (1:8), is parenterally administered over periods ranging from 10 seconds to 20 minutes. Dosing is related to target organ of interest and may range from from 1 $\mu$mol/kg body weight to 100 $\mu$mol/kg body weight of a source of Mn++ ion together with from 2 $\mu$mol/kg body weight to 1400 $\mu$mol/kg body weight of a source of Ca++ ions. Preferably the source of manganese is administered at 2 $\mu$mol/kg body weight to 30 $\mu$mol/kg body weight and the source of calcium is administered at 4 $\mu$mol/kg body weight to 400 $\mu$mol/kg body weight. Most preferably the source of manganese is administered at 3 $\mu$mol/kg body weight to 15 $\mu$mol/kg body weight and the source of calcium is administered at 6 $\mu$mol/kg body weight to 200 $\mu$mol/kg body weight. MRI is performed from during or immediately post dosing to 24 hours post dosing (vascular indications excepted). The rate of administration may be varied to further improve the cardiovascular tolerability of the contrast agent without an adverse effect on image quality, to increase the duration of the vascular phase of the agent, or to increase the dose without reducing the therapeutic index of the agent in order to enable imaging of target organs that accumulate manganese less efficiently than does liver.

Advantages of the invention include: (1) Less of the administered dose is excreted renally (essentially none vs. 15 or so percent for MnDPDP); this effectively reduces the dose of Mn required for optimal image enhancement; (2) The solution relaxivity of manganese salts is maintained; (3) The risk of toxicity associated with the presence of chelator is avoided. For instance, loss of bioactive metals such as plasma Zn through chelation and renal excretion is avoided: (4) Rapid tissue enhancement is achieved relative to Mn chelates, allowing for earlier imaging; (5) Additional indications, for example imaging of tumors, as well as vascular and cardiac imaging are possible; and (6) The cost of the composition is lower than most chelate compositions and most compositions that employ rarer elements, such as gadolinium.

The invention relates to a diagnostic composition comprising a source of a diagnostically effective quantity of Mn++ ion, a source of Ca++ ion and a pharmaceutically acceptable carrier for parenteral administration. The term "diagnostically effective" refers to an amount of Mn ion sufficient to increase the signal-to-noise ratio for MRI of the tissue in question. With present day instrumentation an increase of at least 5% is required to be diagnostically effective. The term "source of Mn++ or Ca++ ion" means any chemical species that can furnish a measurable concentration of Mn++ or Ca++ ion in normal saline or blood. Thus, when the source is a simple salt, soluble at the concentration employed, such as manganese chloride, manganese gluconate, or calcium gluconate, the molar concentration of the salt will be the molar concentration of the Mn++ or Ca++ ion. When the source is a salt or complex that is not fully dissociated at the concentration employed, the molar concentration of Mn++ or Ca++ ions will be less than the molar concentration of the salt or complex, but its effective molarity can be readily calculated from the solubility product of the components by methods well known in the art, and the effective molarity of the metal ion can be experimentally determined with an ion-specific electrode, as well as similar methods well known in the art. It is to be noted that the concentrations of interest in the invention are those of the ions, not the concentrations of the source species, although the two are the same for simple, soluble salts. A soluble salt, for the purpose of the present invention, refers to a salt which is essentially fully dissociated at the concentration being used.

Antioxidants, such as ascorbate, and stabilizers, such as calcium saccharate and borate complexes may be added to the compositions of the invention, as may other substances known in the pharmaceutical art to be useful in parenteral formulations. Formulations for parenteral administration include aqueous and non-aqueous sterile injection solutions which may contain anti-oxidants, buffers, pH modifiers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, water-for-injection (WFI) or the like, immediately prior to use. Extemporaneous injection solutions and suspensions may be prepared from sterile powders and granules according to methods well known in the pharmaceutical art. Sterile solutions of a unit dose for injection are preferred. A preferred composition for one embodiment of the invention is a sterile solution of 25 mM manganese salt and 200 mM calcium salt in WFI adjusted to pH 6.0 to 8.2 with sodium hydroxide and/or hydrochloric acid. About 4% to 8%, preferably 6%, by weight of the calcium is provided by calcium saccharate and the remainder by calcium gluconate or gluceptate.

The source of manganese is preferably administered intravenously at 1 $\mu$mol/kg body weight to 100 $\mu$mol/kg body weight, more preferably at 2 $\mu$mol/kg body weight to 30 $\mu$mol/kg body weight. In many preferred embodiments, the source of manganese is administered intravenously at 3 $\mu$mol/kg body weight to 15 $\mu$mol/kg body weight. Similarly, the source of calcium is preferably administered intravenously at 2 $\mu$mol/kg body weight to 1400 $\mu$mol/kg body weight, more preferably at 4 $\mu$mol/kg body weight to 400 $\mu$mol/kg body weight. In many preferred embodiments, the source of calcium is administered intravenously at 6 $\mu$mol/kg body weight to 200 $\mu$mol/kg body weight.

The terms "tissue", "organ" and "system" are used in their normal sense. Thus, "tissue" refers to such biological materials as gastrointestinal mucosa, tumor and the like. "Organ" refers to such biological organs as the liver, the kidney, the pancreas, the adrenal glands, the heart, the brain, salivary glands, and the uterus. "System" refers to such biological systems as the biliary system, the gastrointestinal system and the cardiovascular or circulatory system.

In accordance with the method of the invention, the source of Mn++ and the source of Ca++ may be administered separately or in a single composition. As will be evident to the person of skill, the administration of a single parenteral dosage form will usually be simplest, but the clinician may employ any means known in the art to achieve the desired ratio of Mn++ to Ca++ in the individual being treated and to achieve the desired level of Mn++ in the tissue, organ or system of interest. As will be seen below, administration of the two ions within 30 minutes of each other will generally be successful, but it is necessary to administer the calcium first, when sequential administration is employed.

EXAMPLE 1

Preparation of Manganese gluconate/Calcium gluconate 1:X

A 27.9 mM Manganese gluconate stock solution was prepared as described below. The Mn gluconate used contained 5.5% water by assay. Ca gluconate and water for injection were added to the stock to prepare solutions of Mn gluconate and Ca gluconate of fixed molar ratio, as noted below. Without the addition of solubility enhancers, the concentration of the prepared solutions was limited to approximately 3% by weight Ca gluconate. The 27.9 mM Mn stock solution was prepared by adding 6.56 g of Mn gluconate to 500 mL of water for injection. Because the stock solution was 27.9 mM, rather than 30.0 mM, the ratios shown below in the examples, tables and figures are not exactly 1:1 etc, but they fall within 10% of the nominal ratio. The conclusions to be drawn are not substantively affected by this discrepancy, and the absolute values may be recalculated by the reader if need be.

Mn/Ca 1:1 - To 50 mL of stock solution add 0.646 g of Ca gluconate.
Mn/Ca 1:2 - To 50 mL of stock solution add 1.292 g of Ca gluconate
Mn/Ca 1:4 - To 50 mL of stock solution add 50 mL of water for injection and 2.582 g of Ca gluconate.
Mn/Ca 1:6 - To 16.6 mL of stock solution add 33.3 mL of water for injection and 1.29 g of Ca gluconate.
Mn/Ca 1:8 - To 12.5 mL of stock solution add 38.5 mL of water for injection and 1.29 g of Ca gluconate.

Alternatively, the desired Mn/Ca compositions can be made by adding Mn gluconate to commercially available Calcium Gluconate for Injection, 10% (232 mM) which contains calcium saccharate as a solubility enhancing agent. For example: Mn/Ca 1:8 [29 mM in Mn, 232 mM in Ca(II)] Ten milliliters of Calcium Gluconate Injection, 10%, is added to 136 mg of Mn gluconate.

EXAMPLE 2

Calcium Gluconate Dose Range in Rabbits

Contrast media of the invention, with molar Ca to Mn ratios of 1:1 to 8:1, prepared according to the description in Example 1, were studied for their effects on systolic blood pressure following intravenous administration in New Zealand White Rabbits. The Mn++ dose for all compositions was held constant at about 30 $\mu$mol/kg, a dose previously shown to induce a minimum 20% drop in systolic blood pressure. Changes in blood pressure were monitored via an in-dwelling femoral artery catheter. Blood pressure baselines were re-established between doses. Table 1 summarizes the findings in a study in which the Ca/Mn ratio was doubled with each successive dose. Table 2 summarizes findings in a second experiment focused on the more effective range of ratios studied in the exploratory experiment. The data presented in Tables 1 and 2 together demonstrate that the combination of Ca and Mn in 2:1 or greater ratio exhibits weaker cardiovascular side effects than intravenously administered Mn. The effect is dose related, as measured by both peak effect and area under the curve, which reflect the extent and duration of the Mn response. Of particular note in these data is the result for the 1:1 Mn/Ca composition, which was substantially similar to that of Mn alone. This result is consistent with the findings of Schaefer et al, and stands in surprising contrast to the results obtained at higher Ca/Mn ratios.

TABLE 1

Normalized Systolic Blood Pressure 0–5 min Post Administration

|  | Peak % Change from Baseline | % Difference Between Mn and Mn plus Ca | Area under Curve | % Difference Between Mn and Mn plus Ca |
|---|---|---|---|---|
| Mn (30 $\mu$mol/kg)* | −27% | NA | −0.96 | NA |
| 1× Ca added | −25% | 7% | −1.04 | −8% |
| 2× Ca added | −17% | 37% | −0.70 | 29% |
| 4× Ca added | −11% | 59% | −0.33 | 66% |
| 8× Ca added | −7% | 74% | −0.24 | 75% |

*Mean Normalized Data (n = 4)

TABLE 2

Normalized Systolic Blood Pressure 0–15 Minutes Post Administration

|  | Peak % Change from Baseline | % Difference Between Mn and Mn plus Ca | Area under Curve | % Difference Between Mn and Mn plus Ca |
|---|---|---|---|---|
| Mn (30 $\mu$mol/kg) | −53% | NA | −6.45 | NA |
| 4× Ca added | −34% | 36% | −4.07 | 37% |
| 6× Ca added | −32% | 40% | −2.86 | 56% |
| 8× Ca added | −23% | 57% | −1.22 | 81% |

FIG. 1 illustrates the change in normalized systolic blood pressure over time for Mn and for several Mn/Ca compositions of different molar ratios, all administered intravenously in the rabbit at a constant Mn++ ion dose of about 30 μmol/kg. The 4:1 mixture of calcium gluconate and manganese gluconate depressed systolic blood pressure only to about half the extent seen with pure manganese gluconate; the 8:1 mixture produced very little and very short lived depression of systolic blood pressure; 6:1 was better than 4:1 and much better than pure manganese gluconate, but not as good as 8:1 in this test.

EXAMPLE 3

Rabbit Confirmatory Study

Table 3 shows data collected in a naive rabbit for Mn dosed at about 30 μmol/kg and Ca at 240 μmol/kg, individually and as a mixture, following the same protocol used in Example 2.

TABLE 3

Blood Pressure Effects for Mn/Ca 1:8 Compared to Mn and Ca Alone

| | Normalized Systolic Blood Pressure | | Normalized Mean Blood Pressure | |
|---|---|---|---|---|
| | Peak % Change from Baseline | Area under Curve (% Difference Between Mn and Mn plus Ca) | Peak % Change from Baseline | Area Under Curve (% Difference Between Mn and Mn plus Ca) |
| Mn (30 μmol/kg) | −15% | −0.90 | −18% | −1.26 |
| Mn/Ca (1:8) | −15% | −0.135 (85%) | −12% | −0.57 (55%) |
| Ca (240 μmol/kg) | +7% | 0.43 | −9% | −0.10 |

Figure 2:
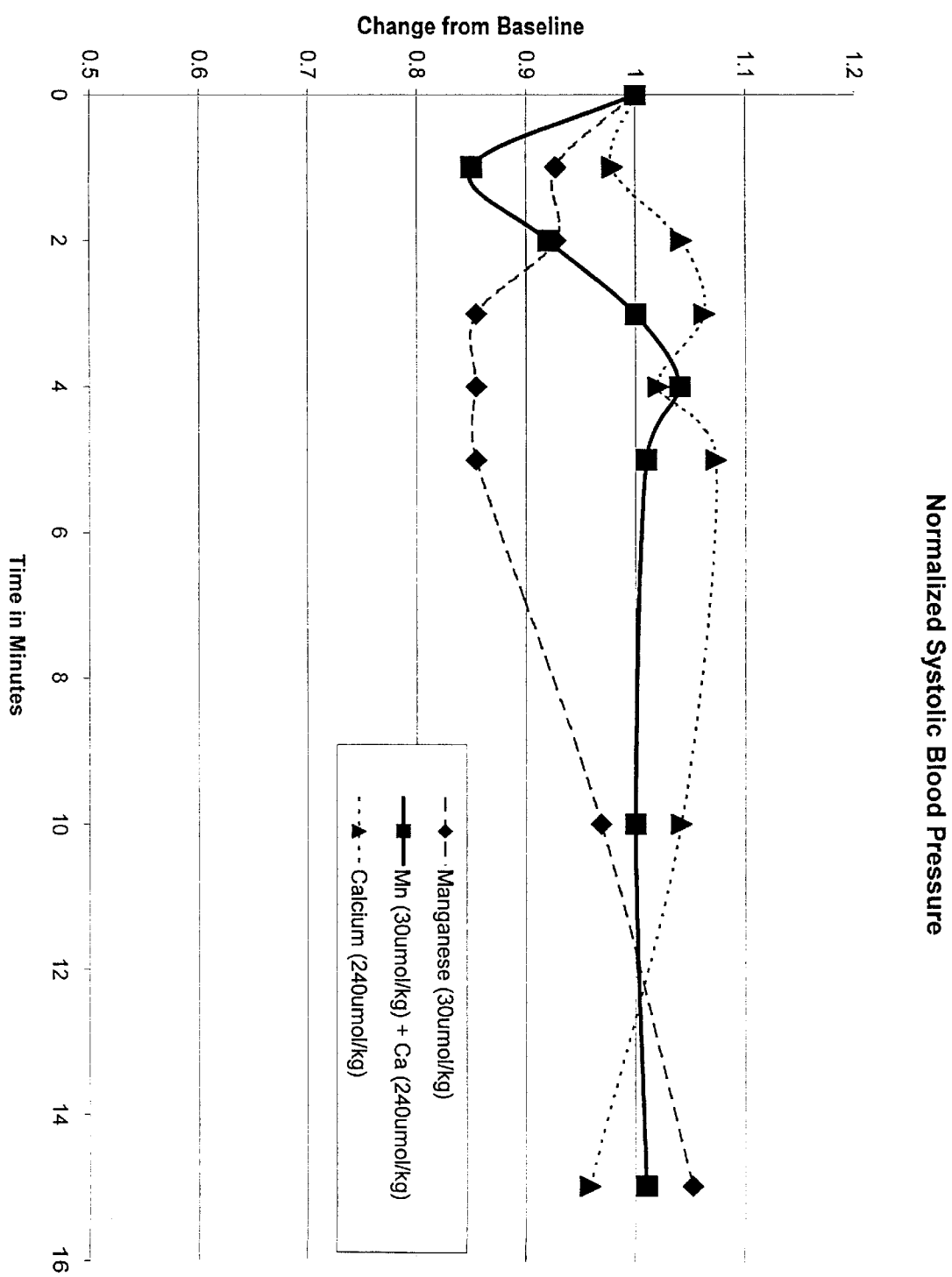
FIG. 2 is also a graph of normalized systolic blood pressure in which the change from baseline (in percent) is plotted as a function of time (in minutes)

The data demonstrate that the cardiovascular effects of the Mn/Ca combination are not predictable from the effects of either agent alone. For example, using area under the curve (AUC) as a measure of both extent and duration of change in systolic blood pressure, one would predict an AUC of −0.47 (by adding 0.43 to −0.90) for the 1:8 Mn/Ca composition; in fact a significantly smaller AUC of −0.135 is seen experimentally. This is clearly visible through examination of FIG. 2, in which the changes in normalized systolic blood pressure for a 1:8 mole ratio mixture of Mn gluconate and Ca gluconate, a representative embodiment of this invention, are compared to the effects noted following intravenous administration of Mn or Ca alone. As in the AUC comparison, the results for the Mn/Ca composition differ from those predictable via simple addition of the individual Mn and Ca curves.

EXAMPLE 4

Mn/Ca compositions in the rat

A 1:8 mole ratio Mn/Ca contrast agent of this invention, prepared according to the description in Example 1, was studied for effects on systolic and mean blood pressure relative to a Mn gluconate control in Wistar rats. Agents were administered intravenously at a Mn dose of 100 μmol/kg. Changes in blood pressure were monitored via an in-dwelling femoral artery catheter. The results, shown in Table 4, confirm that in the rat, as well as the rabbit, the combination of Mn and Ca produces less depression of hemodynamic parameters than does Mn alone, thus permitting the safe administration of a diagnostically effective dose.

TABLE 4

1:8 Mn/Ca, Effect Measured by Peak Change in Pressure and Time-matched AUC's

| | Mn @ 100 umol/kg | Mn @ 100 umol/kg Ca @ 800 umol/kg | % Difference Between Mn and Mn plus Ca |
|---|---|---|---|
| Systolic Pressure, Peak | −36% | −18% | 50% |
| Mean Pressure, Peak | −33% | −23% | 30% |
| Systolic Pressure, AUC | −0.37 | −0.15 | 59% |
| Mean Pressure, AUC | −0.40 | −0.24 | 40% |

EXAMPLE 5

Toxicity as measured by Median Lethal Dose

Acute intravenous toxicity testing in the Swiss Webster mouse was conducted on Mn gluconate, Ca gluconate and a mixture of Mn gluconate and Ca gluconate, 1:10 on a molar basis. All agents were administered via tail vein injection over 30 seconds. For each agent The Median Lethal Dose was established via the Up and Down Method of Bruce (Fundamental and Applied Toxicology 5, 151–157 (1985)). Although the animals were observed for a period of 24 hrs, manganese-related deaths, when they occurred, were noted within minutes of injection, presumably as the result of cardiovascular collapse. The data are shown in Table 5:

TABLE 5

Median Lethal Dose Studies in the Mouse

|  | MLD | Protective Effect** |
|---|---|---|
| Mn | 138 umol/kg Mn | 0 |
| Mn/Ca (1:10) | 220 umol/kg Mn | 60% Based on Mn |
| Ca | 1819 umol/kg Ca | NA |

**[(MLD/Mn or Ca MLD) − 1] × 100%

EXAMPLE 6

Efficacy Studies, Rabbit Liver Imaging

Pre and post-contrast axial T1-weighted spin-echo and spoiled gradient echo images of the liver were obtained in two rabbits. The post contrast images were obtained up to 30 minutes after injection of Mn/Ca (1:8) (10 μmol/kg Mn). Images were obtained on a GE Signa Imager operating at 1.5 T. Signal intensity and signal-to-noise ratios were determined via region of interest (ROI) analysis. Good enhancement of the liver was seen in all cases, as shown in Table 6 below. In addition, the data presented in FIG. 3, collected via ROI analysis of the liver as seen in the vascular images obtained in Example 7, show that Mn/Ca (1:8) provides fairly rapid enhancement of the liver, with measured signal to noise greater than 50% of the maximal SNR by the end of the one minute injection of contrast.

TABLE 6

Contrast Enhanced Liver Imaging, Mn/Ca (1:8)

| | Mn/Ca (1:8): Liver Imaging | | | |
|---|---|---|---|---|
| | Liver Signal Intensity | | Liver Signal to Noise | |
| | Pre | Post | Pre | Post |
| Rabbit 1: T1 Spin Echo | 404 | 635 | 9.4 | 12.0 |
| Spoiled Gradient Echo | 688 | 1012 | 13.1 | 16.0 |
| Rabbit 2: T1 Spin Echo | 544 | 769 | 10.1 | 13.9 |
| Spoiled Gradient Echo | 705 | 1170 | 6.9 | 15.5 |

EXAMPLE 7

Efficacy Studies, Rabbit Vascular Imaging

The blood phamacokinetics of Mn/Ca (1:8) were examined by MRI in the rabbit. The contrast agent was administered intravenously in the ear vein over 1 minute at a dose of 10 μmol/kg Mn. Blood samples (3mL each in heparinized tubes) were taken from the ear artery prior to and immediately, 2, 10, 20, 30 and 60 minutes post administration of contrast. The tubes were imaged in cross-section via T1-weighted spin echo imaging (TR=300, TE=15,4NEX, FOV=8) on a GE Signa 1.5 T Imager. The signal intensity data, shown in Table 7, demonstrate pharmacokinetics consistent with those found for Mn++, when measured with a $^{56}$Mn tracer. (Borg, D. C.; Cotzias, G. C. J Clin Invest. 37:1269)

TABLE 7

Vascular Image Enhancement with Mn/Ca (1:8)

Mn/Ca 1:8 Evaluation of Vascular Enhancement over Time

| | Blood Signal Intensity | Percent Enhancement of the Blood |
|---|---|---|
| Pre-Contrast | 363 | 0% |
| Immediately Post Contrast | 733 | 102% |
| 2 Min Post Contrast | 594 | 64% |
| 10 Min Post Contrast | 464 | 28% |
| 20 Min Post Contrast | 419 | 15% |

EXAMPLE 8

Ex-vivo imaging—Saline vs. Whole Blood

The T1 shortening seen with Mn/Ca (1:8) in saline was compared to that seen in blood. Tubes of saline and blood (3 mL each) were spiked with 100%, 50% and 10% of the intravascular concentration of Mn/Ca (1:8) that would be expected if it were administered as a bolus at a dose of 10 μmol/kg Mn. For comparison, Gd DTPA was spiked in 3 mL of saline and blood at 100% of the expected intravascular concentration following bolus dosing at 100 μmol/kg, a dose typically used in the clinic for vascular imaging. The tubes were imaged in cross section via T1-weighted spin echo imaging (TR=300, TE=15,4NEX, FOV=8) on a GE Signa 1.5 T Imager. The results are summarized in Table 8.

TABLE 8

MRI Signal Intensity in Saline and Whole Rabbit Blood Spike with Mn/Ca (1:3) or Gd DTPA

| | Signal Intensity in Saline | Signal Intensity in Blood | Percent Enhancement in Blood | Blood/Saline Signal Intensity |
|---|---|---|---|---|
| Mn, 0% | NA | 363 | 0% | NA |
| Mn, 10% | 262 | 768 | 112% | 2.93 |
| Mn, 50% | 563 | 1658 | 357% | 2.94 |
| Mn, 100% | 685 | 1817 | 401% | 2.65 |
| Gd, 100% | 2162 | 1449 | 299% | 0.67 |

It is interesting to note the significant increase in signal intensity seen for Mn/Ca (1:8) in the blood relative to saline. For instance, the signal intensity seen for Mn 10% in blood is essentially equivalent to that seen for Mn 100% in saline. This indicates interaction with blood components. This increase in efficacy is not seen with Gd DTPA, which demonstrates reduced signal enhancement in blood relative to saline. The signal intensity seen for Mn/Ca (1:8) at 50% of the expected blood concentration was greater than that seen for Gd DTPA at 100% of its expected blood concentration, despite that fact that Gd DTPA was administered at 20 times the Mn/Ca dose on molar basis. This corresponds to at least a 40-fold efficacy advantage over Gd DTPA in blood. An even greater molar efficacy advantage is expected over Mn administered as a chelate, since chelated Mn has a lower relaxively than does chelate Gd. For example MnDPDP, which does not bind to plasma proteins, has a solution R1 of 1.90 $s^{-1}mM^{-1}$ at 40° C. and 20 MHz. GdDTPA has an R1 of 3.84 $s^{31}$ $^{1}mM^{-1}$ under similar conditions.

We claim:

1. A diagnostic composition comprising a source of a diagnostically effective quantity of Mn++ ion, a source of Ca++ ion and a pharmaceutically acceptable carrier for parenteral administration, wherein said Ca++ ion is present in a molar ratio of from 2:1 to 40:1 with respect to said Mn++ ion.

2. A diagnostic composition according to claim 1 wherein said source of Mn++ is a manganese salt chosen from manganese acetate, chloride, gluconate, gluceptate, lactate and sulfate or a mixture thereof.

3. A diagnostic composition according to claim 2 wherein said source of Mn++ is manganese gluconate or manganese gluceptate.

4. A diagnostic composition according to claim 1 wherein said source of Ca++ is a calcium salt chosen from calcium acetate, chloride, gluconate, gluceptate, and lactate or a mixture thereof.

5. A diagnostic composition according to claim 4 wherein said source of Ca++ is calcium gluconate or calcium gluceptate.

6. A diagnostic composition according to claim 1 wherein said molar ratio of calcium to manganese is from 4:1 to 20:1.

7. A diagnostic composition according to claim 6 wherein said molar ratio of calcium to manganese is from 8:1 to 10:1.

8. A diagnostic composition according to claim 1 additionally comprising an antioxidant.

9. A diagnostic composition according to claim 8 wherein said antioxidant is ascorbate.

10. A diagnostic composition according to claim 1 additionally comprising a stabilizer.

11. A diagnostic composition according to claim 10 wherein said stabilizer is calcium saccharate or a borate complex.

12. A unit dosage form comprising a salt of manganese containing from 5 mg to 200 mg of manganese, a salt of calcium containing from 20 mg to 3 g of calcium, and a vehicle suitable for parenteral injection.

13. A unit dosage form according to claim 12 comprising from 60 mg to 1.5 g of manganese gluconate or manganese gluceptate and from 250 mg to 32 g of calcium gluconate or gluceptate.

14. A unit dosage form according to claim 13 in a water-for-injection vehicle adjusted to pH 6.0 to 8.2, additionally comprising calcium saccharate in an amount such that about 4% to about 8% of the calcium present in the dosage form is in the form of calcium saccharate.

15. A method for enhancing a magnetic resonance image of a mammalian tissue, organ or system comprising administering to a mammal a diagnostically effective amount of a source of Mn++ ion together with from 2 to 200 molar equivalents of a source of Ca++ ions.

16. A method according to claim 15 wherein said source of Mn++ is a manganese salt chosen from manganese acetate, chloride, gluconate, gluceptate, lactate and sulfate or a mixture thereof and said source of Ca++ is a calcium salt chosen from calcium acetate, chloride, gluconate, gluceptate, and lactate or a mixture thereof.

17. A method according to claim 16 wherein said source of Mn++ is manganese gluconate or manganese gluceptate and said source of Ca++ is calcium gluconate or calcium gluceptate.

18. A method according to claim 15 wherein the molar ratio of calcium to manganese is from 4:1 to 20:1.

19. A method according to claim 15 wherein the molar ratio of calcium to manganese is from 8:1 to 10:1.

20. A method for enhancing a magnetic resonance image of a mammalian tissue, organ or system comprising administering to a mammal from 1 $\mu$mol/kg body weight to 100 $\mu$mol/kg body weight of a source of Mn++ ion together with from 2 $\mu$mol/kg body weight to 1400 $\mu$mol/kg body weight of a source of Ca++ ions.

21. A method according to claim 20 wherein said source of manganese and said source of calcium are administered intravenously.

22. A method according to claim 21 wherein said source of manganese is administered at 2 $\mu$mol/kg body weight to 30 $\mu$mol/kg body weight and said source of calcium is administered at 4 $\mu$mol/kg body weight to 400 $\mu$mol/kg body weight.

23. A method according to claim 22 wherein said source of manganese is administered at 3 $\mu$mol/kg body weight to 15 $\mu$mol/kg body weight and said source of calcium is administered at 6 $\mu$mol/kg body weight to 200 $\mu$mol/kg body weight.

24. A method according to claim 20 wherein the tissue, organ or system is chosen from liver, kidney, pancreas, adrenal glands, heart, brain, salivary glands, gastrointestinal mucosa, uterus, the biliary system and tumor.

25. A method according to claim 20 wherein the tissue, organ or system is the circulatory system.

26. A method according to claim 20 wherein the source of Mn++ is administered separately within 30 minutes following the administration of the source of Ca++.

27. A method according to claim 20 wherein the source of Mn++ and the source of Ca++ are administered simultaneously.

* * * * *

UNITED STATES PATENT AND TRADEMARK OFFICE
CERTIFICATE OF CORRECTION

PATENT NO. : 5,980,863
DATED       : November 09, 1999
INVENTOR(S): Harnish et al.

It is certified that error appears in the above-identified patent and that said Letters Patent is hereby corrected as shown below:

IN THE CLAIMS:

Claim 12, Col. 13, line 49, after "injection" insert --, wherein said calcium ion is present in the molar ratio from 2:1 to 40:1 with respect to said manganese ion--.

Claim 15, Col. 14, line 8, after "ions" insert --, wherein said calcium ion is present in the molar ratio from 2:1 to 40:1 with respect to said manganese ion--.

Claim 20, Col. 14, line 28, after "ions" insert --, wherein said calcium ion is present in the molar ratio from 2:1 to 40:1 with respect to said manganese ion--.

Signed and Sealed this

First Day of August, 2000

Attest:

Q. TODD DICKINSON

*Attesting Officer*        *Director of Patents and Trademarks*